(12) United States Patent
Parrish (10) Patent No.: US 7,805,783 B2
(45) Date of Patent: Oct. 5, 2010

(54) PROCEDURE RADIOGRAPH ORIENTATION DEVICE AND METHODS OF USE

(76) Inventor: Rob G. Parrish, P.O. Box 130507, Houston, TX (US) 77219

( * ) Notice: Subject to any disclaimer, the term of this patent is extended or adjusted under 35 U.S.C. 154(b) by 536 days.

(21) Appl. No.: 11/891,384

(22) Filed: Aug. 9, 2007

(65) Prior Publication Data

US 2009/0043193 A1 Feb. 12, 2009

(51) Int. Cl.
*A61B 6/04* (2006.01)
*A61G 13/08* (2006.01)

(52) U.S. Cl. .............................. 5/601; 5/600; 5/236.1; 378/209

(58) Field of Classification Search ............ 5/601, 5/600, 632, 630, 236.1, 238; 378/209, 208, 378/205, 200, 177; 297/452.63
See application file for complete search history.

(56) References Cited

U.S. PATENT DOCUMENTS

| 254,677 | A | * | 3/1882 | Moore | 5/120 |
| 295,839 | A | * | 3/1884 | Toffler | 160/231.1 |
| 390,393 | A | * | 10/1888 | Norris | 5/120 |
| 673,580 | A | * | 5/1901 | Lustig | 160/231.1 |
| 1,500,338 | A | * | 7/1924 | Shuman | 297/276 |
| 2,551,976 | A | * | 5/1951 | Smith | 5/630 |
| 2,745,473 | A | * | 5/1956 | Boland | 297/230.1 |
| 3,634,685 | A | | 1/1972 | Orwig | |
| 3,940,619 | A | | 2/1976 | Ellingson et al. | |
| 4,192,547 | A | * | 3/1980 | Geier | 297/452.63 |
| 4,244,622 | A | * | 1/1981 | Simpson | 297/273 |
| 5,287,546 | A | | 2/1994 | Tesic et al. | |
| 6,623,081 | B2 | * | 9/2003 | Snyders | 297/452.63 |
| 7,540,661 | B2 | * | 6/2009 | Hornig | 378/209 |
| 2004/0098803 | A1 | | 5/2004 | Schindler | |
| 2007/0003022 | A1 | * | 1/2007 | Hornig | 378/209 |
| 2009/0043193 | A1 | * | 2/2009 | Parrish | 600/426 |

OTHER PUBLICATIONS

Kim Jung Tae (Authorized Officer), International Searching Authority/Korea, International Search Report, Feb. 11, 2009, 3 pages, ISA/KR, Korean Intellectual Property Office, Republic of Korea.
Kim Jung Tae (authorized officer), International Searching Authority/Korea, Written Opinion of the International Searching Authority, Feb. 11, 2009, 3 pages, ISA/KR, Korean Intellectual Property Office, Republic of Korea.

* cited by examiner

*Primary Examiner*—Robert G Santos
(74) *Attorney, Agent, or Firm*—Robert C. Curfiss (57) ABSTRACT

Procedure radiograph orientation devices and methods of use are provided for stabilization and orientation of a patient's anatomy for a variety of surgical interventions. Additionally, devices of the present invention aid in orienting radiographic imaging devices through the inclusion of radiopaque fiducials so as to optimize radiographic images by providing radiographic reference landmarks.

An example of the present invention includes a rostral base plate, a plurality of support slats, and a caudal base plate, these components being adapted to pivot about one another or in certain embodiments, adapted to pivot about a series of spacers. One or more tension wires extend through the slats and base plates, joining the elements. The devices may be secured in various configurations by increasing the tension of the tension cable(s). Visual sighting or aiming devices may also be included in certain embodiments. Certain embodiments may include a rigid base plate having radiopaque fiducials.

2 Claims, 6 Drawing Sheets

PROCEDURE RADIOGRAPH ORIENTATION DEVICE AND METHODS OF USE

BACKGROUND

The present invention generally relates to procedure radiograph orientation devices and more particularly, to procedure radiograph orientation devices utilizing radiopaque fiducials and methods of use.

During various types of medical interventions, orthopedic surgery, and spine surgery, it is important to keep a portion of a patient's anatomy aligned and oriented in a particular way to optimally perform the intervention or surgery. Additionally, during various interventions and surgeries, it is often desired to adjust the alignment or orientation of a portion of a patient's anatomy. Example of medical interventions, orthopedic surgeries, and spine surgeries requiring proper alignment and orientation of a patient include, but are not limited to anterior spine operations, particularly lumbar and cervical discectomy and fusion or discectomy and arthroplasty (e.g. artificial discs). In many of these orthopedic operations, it is important to keep the curvature of the spine in a normal anatomical alignment or otherwise adjusted in a desired orientation. As spine interventions become more advanced, surgical and medical interventions are requiring a higher level of precision and accuracy in the placement and positioning of a patient's anatomy. Examples of certain types of cervical interventions are disclosed in U.S. patent application Ser. No. 11/643,536, titled "Intervertebral Disc Spacer," the entirety of which is hereby incorporated by reference. Other types of medical interventions such as orthopedic knee replacement or certain types of back surgery require a precise alignment and orientation of a portion of a patient's anatomy.

Common practice in such interventions is to position or stabilize a patient's anatomy with rolled linens or fixed cushions. For example, rolled linens or fixed cushions are commonly used to bolster a patient's spine during certain types of intervertebral disc replacement surgeries. Rolled linens and cushions, however, lack the ability to be easily custom-adjusted to each patient's particular anatomy. Usually, the rolled linens and fixed cushions must be removed from under the patient's neck, adjusted, and reinserted to adjust the placement and orientation of the patient's spine. This method of adjustment is cumbersome and can cause further aggravation to a patient's condition. Additionally, this method of supporting a patient's anatomy is not conducive to making fine adjustments of the patient's position and orientation, such as the need to shift the patient's neck 1 mm upwards from the operating table.

In addition to providing support to a patient's spine anatomy, medical interventions and surgeries of the spine also require accurate and precise aiming of radiographic imaging devices such as fluoroscopes. Failure to accurately align a fluoroscope while obtaining radiographic images can result in imperfectly placed or misaligned spine implants, in addition to internal incisions slightly offset from the desired location. Conventional methods of aiming radiographic devices involve essentially "eyeballing" or estimating orientation based on visual cues to obtain the desired image. Physicians also use the patient's anatomy (e.g. the anatomy of the spine) to determine proper orientation of the radiographic imaging device. For example, the orientation of the anatomy of a patient's spine on a radiographic image can provide a physician with anatomical reference points for adjusting the patient's orientation for optimal cervical interventions. Often, however, a patient's anatomy is not perfectly symmetrical and this anatomical asymmetry results in slightly or in some instances, grossly misorienting or misaiming the radiographic imaging device. As medical interventions and surgeries become more advanced and sophisticated, the need for accurate and precise adjustments are increasing in importance. Therefore, reduced tolerances of error in positioning and orientating a patient's anatomy during orthopedic interventions are becoming more critical.

Thus, conventional methods of aligning radiographic imaging devices and conventional methods for stabilizing patients' spines are unsatisfactory for many types of medical and surgical interventions. Accordingly, it would be desirable to improve and/or replace conventional devices so as to address one or more disadvantages of the prior art.

SUMMARY

The present invention generally relates to procedure radiograph orientation devices and more particularly, to procedure radiograph orientation devices utilizing radiopaque fiducials and methods of use.

An example of a procedure radiograph orientation device comprises an elongated rostral base plate having a first elongated edge and a second elongated edge with an aperture extending therebetween, wherein the second elongated edge thereof is adapted to receive at least partially a spacer; a caudal base plate having a first elongated edge and a second elongated edge with an aperture extending therebetween, wherein the first elongated edge thereof is adapted to receive at least partially a spacer; a plurality of elongated support slats, each support slat having a first elongated edge and a second elongated edge with an aperture extending therebetween, wherein the first and second elongated edges are adapted to receive at least partially a spacer; a first tension cable extending through the apertures of the elongated rostral base plate, the plurality of elongated support slats, and the elongated caudal base plate; a first tension adjuster for adjusting a tension of the first tension cable; wherein the plurality of elongated support slats are disposed successively adjacent one another between the rostral base plate and the caudal base plate so that the elongated edges thereof are substantially parallel, the elongated support slat closest to the rostral base plate being a first support slat and the elongated support slat closest to the caudal base plate being a last support slat; a plurality of spacers wherein each spacer is disposed between each of the plurality of support slats, between the rostral base plate and the first support slat, and between the last support slat and the caudal base plate; wherein one or more of the plurality of spacers are radiopaque, the one or more radiopaque spacers being referred to as horizontal fiducials; and a first vertical fiducial secured to one of the following: the rostral base plate, the caudal base plate, and at least one of the elongated support slats, wherein the first vertical fiducial is radiopaque.

Another example of a procedure radiograph orientation device comprises a base plate having an x-axis and a y-axis, the y-axis being perpendicular to the x-axis wherein the base plate is substantially radiolucent; a plurality of horizontal fiducials fixed to the base plate wherein each horizontal fiducial is substantially parallel to the x-axis of the base plate wherein the horizontal fiducials are substantially radiopaque; and a plurality vertical fiducials fixed to the base plate wherein the vertical fiducials are substantially parallel to the y-axis wherein the vertical fiducials are substantially radiopaque.

An example of a method for stabilizing and orienting a patient and a radiographic imaging device for a surgical intervention comprises: providing a procedure radiograph orientation device comprising: an elongated rostral base plate having a first elongated edge and a second elongated edge with an aperture extending therebetween, wherein the second elongated edge thereof is adapted to receive at least partially a spacer; a caudal base plate having a first elongated edge and a second elongated edge with an aperture extending therebetween, wherein the second elongated edge thereof is adapted to receive at least partially a spacer; a plurality of elongated support slats, each elongated support slat having a first elongated edge and a second elongated edge with an aperture extending therebetween, wherein the first and second elongated edges are adapted to receive at least partially a spacer; a first tension cable extending through the apertures of the elongated rostral base plate, the plurality of elongated support slats, and the elongated caudal base plate; a first tension adjuster for adjusting a tension of the first tension cable; wherein the plurality of elongated support slats are arranged sequentially along the length of the first tension cable between the rostral base plate and the caudal base plate, the elongated support slat closest to the rostral base plate being a first support slat and the elongated support slat closest to the caudal base plate being a last support slat; a plurality of spacers wherein each spacer is disposed between each of the plurality of elongated support slats, between the rostral base plate and the first support slat, and between the last support slat and the caudal base plate; wherein one or more of the plurality of spacers are radiopaque, the one or more radiopaque spacers being referred to as horizontal fiducials; and a first vertical fiducial wherein the first vertical fiducial is radiopaque; adapting the procedure radiograph orientation device to a supporting orientation; and adjusting the tension of the tension cable via the tension adjuster so as to secure the procedure radiograph orientation device in the supporting orientation.

Yet another example of a procedure radiograph orientation device comprises an elongated rostral base plate having a first elongated edge and a second elongated edge with an aperture extending therebetween; a caudal base plate having a first elongated edge and a second elongated edge with an aperture extending therebetween, wherein the first elongated edge thereof is substantially convex; a plurality of elongated support slats, each support slat having a first elongated edge and a second elongated edge with an aperture extending therebetween, wherein the first elongated edge is substantially convex; a first tension cable extending through the apertures of the elongated rostral base plate, the plurality of elongated support slats, and the elongated caudal base plate; a first tension adjuster for adjusting a tension of the first tension cable; and wherein the plurality of elongated support slats are disposed successively adjacent one another between the rostral base plate and the caudal base plate so that the elongated edges thereof are substantially parallel, the elongated support slat closest to the rostral base plate being a first support slat and the elongated support slat closest to the caudal base plate being a last support slat.

The features and advantages of the present invention will be apparent to those skilled in the art. While numerous changes may be made by those skilled in the art, such changes are within the spirit of the invention.

BRIEF DESCRIPTION OF THE DRAWINGS

A more complete understanding of the present disclosure and advantages thereof may be acquired by referring to the following description taken in conjunction with the accompanying figures, wherein.

While the present invention is susceptible to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF PREFERRED EMBODIMENTS

The present invention generally relates to procedure radiograph orientation devices and more particularly, to procedure radiograph orientation devices utilizing radiopaque fiducials and methods of use.

Generally, the present invention provides stabilization of a portion of a patient's anatomy, including in certain embodiments, providing stabilization of a patient's cervical and/or lumbar vertebrae through the use of a procedure radiograph orientation device. In this and other embodiments, the present invention aids in the aiming of radiographic imaging devices through the use of horizontal and vertical fiducials. Methods of use are also provided herein.

Advantages of the devices of the present invention include, but are not limited to, the ability to provide stabilization of a patient's spine, the ability to easily make fine, custom adjustments to the position and orientation of a patient's anatomy, and the ability to secure a patient's anatomy in a particular orientation once a desired orientation is achieved. Additionally, devices of the present invention, in some embodiments, include certain features which allow radiographic imaging devices to be accurately and precisely aimed and oriented in relation to the patient's supported anatomy.

To facilitate a better understanding of the present invention, the following examples of certain embodiments are given. In no way should the following examples be read to limit, or define, the scope of the invention.

Figure 1:
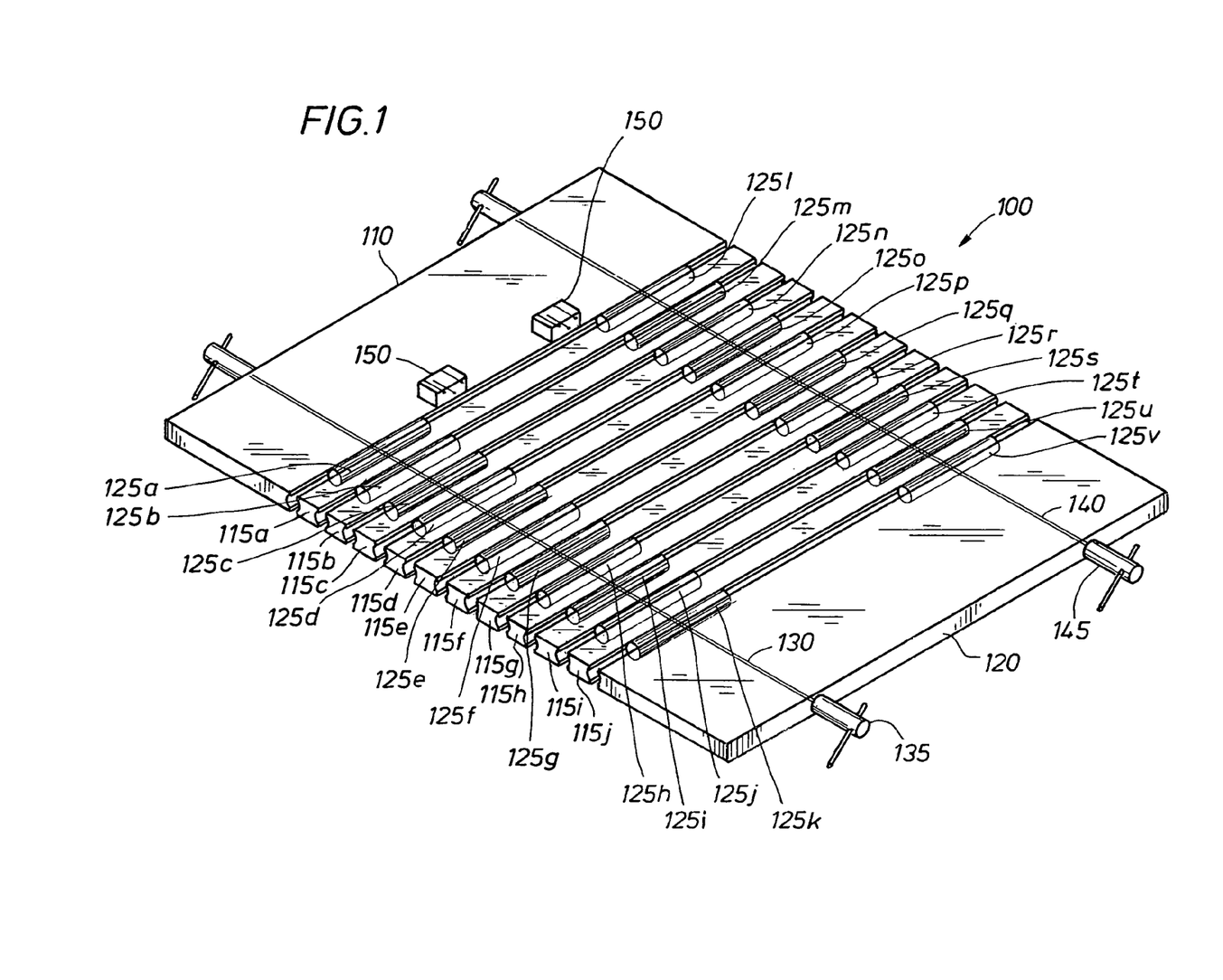
FIG. 1 illustrates a perspective view of an example of a procedure radiograph orientation device.

FIG. 1 illustrates a perspective view of an example of a procedure radiograph orientation device. Procedure radiograph orientation device 100 is comprised of a rostral base plate 110, a plurality of elongated support slats 115a-115j, a plurality of spacers 125a-125v, caudal base plate 120, a first tension cable 130, a second tension cable 140, first and second cable tension adjusters 135 & 145, and vertical fiducials 150.

Procedure radiograph orientation device 100 provides support for a patient undergoing a medical or surgical intervention, including, but not limited to, orthopedic operations, such as cervical or lumbar interventions. In particular, in one example of use of device 100, a patient may rest a portion of his body on device 100 with the patient's body substantially parallel to the first and second tension cables 135 & 145, wherein the patient's head is situated substantially towards rostral base plate 110, and wherein the patient's tailbone is situated towards caudal base plate 120.

In this embodiment, ten elongated support slats 115a-115j are depicted, with elongated support slat 155A being referred to here as the first support slat and elongated support slat 115j being referred to here as the last support slat. As would be recognized by one skilled in the art with the benefit of this disclosure, any number of elongated support slats may be used in the various embodiments of device 100.

Spacers 125a & 125l are disposed between rostral base plate 110 and first support slat 115a. Spacers 125b-125u are disposed between elongated support slats 115a-115j. Spacers 125k & 125v are disposed between last support slat 115j and caudal base plate 120.

First and second tension cables 135 & 145 extend through rostral base plate 110, elongated support slats 115a-115j, spacers 125a-125v, and caudal base plate 120. As shown in FIG. 1, first and second tension cables 130 & 140 extend through the thickness of base plates 110 & 120 and through the thickness of elongated support slats 115a-115j. Optionally, tension cables 130 & 140 may also extend through spacers as depicted in FIG. 1. In this way, base plates 110 & 120, elongated support slats 115a-115j, and spacers 125a-125v are joined and held together by first and second tension cables 130 & 140.

Tension adjusters 135 & 145 may be used to adjust the tension of tension cables 130 & 140. Adjusting the tension of tension cables 130 & 140 varies the longitudinal stress applied to each tension cable 130 & 140. A loose tension on tension cables 130 & 140 allows rostral base plate 110, elongated support slats 115a-115j, and caudal base plate 120 to pivot about spacers 125a-125v freely. Tightening the tension of tension cables 130 & 140 increasingly constrains the free pivoting of support slats 115a-115j around spacers 125a-125v. Tension cables 130 & 140 may be tightened with sufficient tension to maintain procedure radiograph orientation device 100 in a desired fixed orientation as will be later discussed with reference to FIG. 4.

Certain portions of procedure radiograph orientation device 100 may be radiolucent and certain portions of procedure radiograph orientation device 100 may be radiopaque. As used herein, the term "radiolucent" refers to a property of a material that renders the material substantially transparent to X-rays or other forms of radiation whereas the term "radiopaque" refers to a property of a material that renders the material not transparent to or substantially opaque to X-rays or other forms of radiation. In this way, radiopaque elements of device 100 appear on radiographic images and thus serve as useful radiographic reference landmarks for the positioning and orientating of radiographic imaging devices and for properly positioning a patient's anatomy.

In this embodiment, rostral base plate 110, elongated support slats 115a-115j, and caudal base plate 120 are substantially radiolucent. In certain embodiments, only a portion of rostral base plate 110, elongated support slats 115a-115j, and caudal base plate 120 are substantially radiolucent. By being radiolucent, rostral base plate 110, elongated support slats 115a-115j, and caudal base plate 120 appear on X-ray or other radiological images as substantially transparent (or depending on the parameters and conditions of the imaging technology and the transparency of the materials used, the radiolucent materials may be completely absent from an X-ray image or other radiological images). Optionally, certain spacers may be radiolucent whereas others are substantially radiopaque. In this embodiment, spacers 125a, 125c, 125e, 125g, 125i, 125k, 125m, 125o, 125q, 125s, & 125u are substantially radiopaque whereas spacers 125b, 125d, 125f, 125h, 125j, 125l, 125n, 125p, 125r, 125t, & 125v are substantially radiolucent. In this way, every other spacer appears on a radiographic image as radiopaque. This alternating radiographic transparency of spacers 125a-125v allows, among other benefits, for easier orientation and landmark identification of procedure radiograph orientation device 100 when using radiographic imaging. Thus, radiopaque spacers 125b, 125d, 125f, 125h, 125j, 125l, 125n, 125p, 125r, 125t, & 125v, referred to herein as horizontal fiducials, provide fixed horizontal references for orienting a radiographic imaging device with respect to device 100.

Vertical fiducials 150 are fixed radiopaque vertical lines, wires, markers, or other structures that provide a fixed vertical reference for alignment and orientation of a radiographic imaging device with respect to procedure radiograph orientation device 100. The appearance of vertical fiducials on a radiographic image varies depending on the orientation of a radiographic imaging device relative to device 100. In this way, vertical fiducials of device 100 aid users of device 100 in orientating the angle and orientation of radiographic imaging devices with respect to the patient by providing radiographic reference landmarks.

In addition to being radiolucent, certain components of procedure radiograph orientation device 100 may also be optically transparent to allow for easier visual identification of the radiolucent components of procedure radiograph orientation device 100. Likewise, certain components of procedure radiograph orientation device 100 may also be optically opaque to allow for easier visual identification of the radiopaque components of procedure radiograph orientation device 100. In this way, the radiolucent components are transparent while the radiopaque components are opaque or non-transparent. This configuration may be used to visually orient an x-ray machine beam utilizing the aiming light on some radiographic devices.

The components of procedure radiograph orientation device 100 may be made of any material known in the art that is capable of providing support for a patient during normal operation, that does not cause an adverse reaction to the skin upon human contact, and that provides the desired radiographic and/or visual properties of radiotranslucency and radiopaqueness, including, but not limited to, acrylics and acrylic derivatives, methacrylates and methacrylate derivatives, polycarbonates, clear PVC, transparent PETG (glycol modified polyethylene terphthalate), wood, wood-like materials, wood-derivative materials, composite materials, known plastics in the art, known metals and alloys in the art, particularly lightweight alloys, or any combination thereof. In certain embodiments, light weight materials are preferred for convenience of handling.

Figures 2A, 2B, 2C, 3A, 3B, 3C:
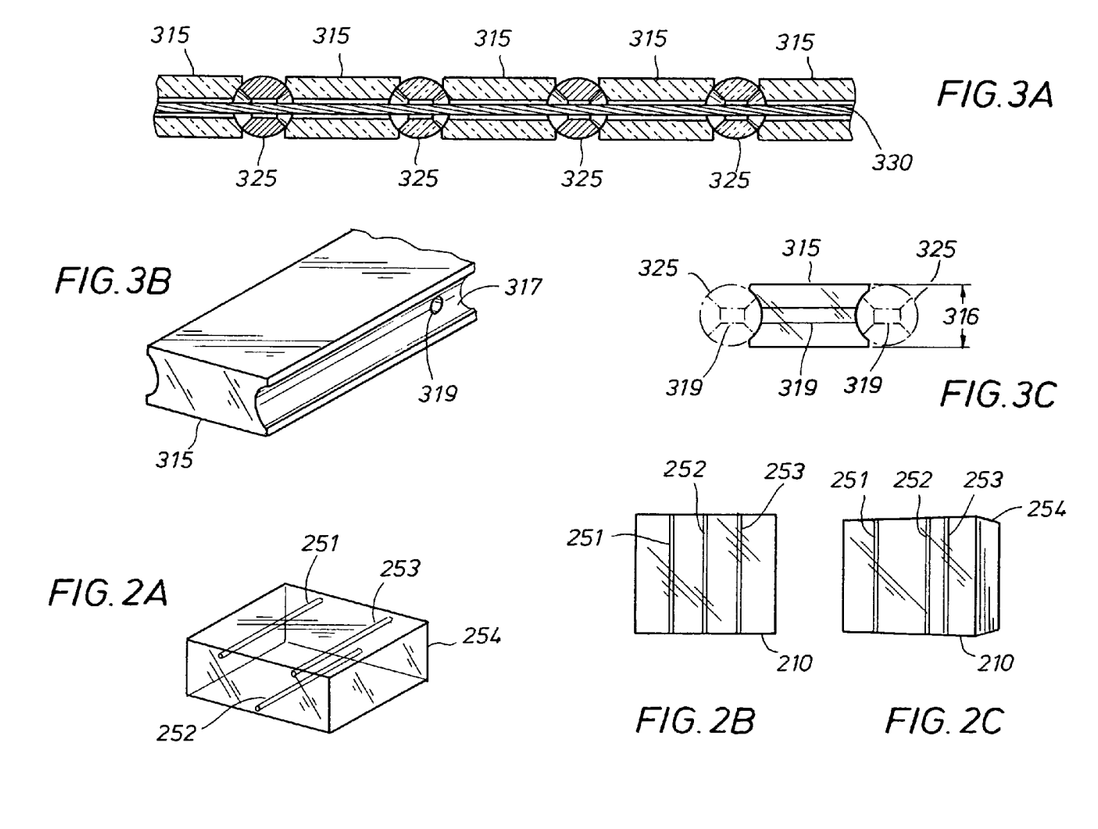
FIG. 2A illustrates a perspective view of vertical fiducials in accordance with one embodiment of the present invention.
FIG. 2B illustrates a top view of vertical fiducials in accordance with one embodiment of the present invention.
FIG. 2C illustrates an offset top view of vertical fiducials in accordance with one embodiment of the present invention.
FIG. 3A illustrates a cross-sectional view of an example of plurality of an elongated support slats operably interacting via a tension cable.
FIG. 3B illustrates a perspective view of an example of one end of an elongated support slat.
FIG. 3C illustrates a cross-sectional view of an example of one end of an elongated support slat

FIG. 2A illustrates a perspective view of vertical fiducials in accordance with one embodiment. In certain embodiments, vertical reference fiducials 251 & 253 and centering vertical fiducial 252 reside in a fiducial retainer 254. Fiducial retainer 254 is radiolucent whereas vertical fiducials 251, 252, & 253 are substantially radiopaque. Thus, vertical fiducials 251, 252, & 253 appear on radiographic images and in this way, provide radiographic reference landmarks. In certain embodiments, as shown here, vertical fiducials are oriented as substantially perpendicular to horizontal fiducials 125b, 125d, 125f, 125h, 125j, 125l, 125n, 125p, 125r, 125t, & 125v. Although vertical fiducials 251 & 253 are depicted here as residing in fiducial retainer 254, which is in turn affixed to device 200, it is recognized that vertical fiducials 251, 252, & 253 could reside directly in a rostral base plate, directly in one or more support slats, directly in a caudal base plate, in any component of device 200, or any combination thereof. The term, "secured to," as used herein with respect to the vertical fiducials includes fixing the vertical fiducials to the surface of any component of the procedure radiograph orientation device and/or situating the vertical fiducials directly within a component of the procedure radiograph orientation device. For example, vertical fiducials 251, 252, & 253 may reside directly in a base plate, in one or more elongated slats, or in any combination thereof.

As can be seen in FIG. 2A, vertical reference fiducials 251 & 253 reside in the same plane whereas centering vertical fiducial 252 resides in a plane offset from the plane of vertical reference fiducials 251. Offsetting centering vertical fiducial 252 from the plane of vertical reference fiducials 251 & 253 allows for a parallax effect between centering vertical fiducial 252 and vertical reference fiducials 251 & 253. That is, because centering vertical fiducial 252 is offset and resides in a different plane than the plane of vertical reference fiducials 251 & 253, the relative apparent position of centering vertical fiducial 252 in relation to vertical reference fiducials 251 & 253 will change depending upon the angle from which vertical fiducials 251, 252, & 253 are viewed. Thus, in a two-dimensional image of vertical fiducials 251, 252, & 253, centering vertical fiducial 252 will appear at varying distances relative to vertical reference fiducials 251 & 253 depending on the angle from which vertical fiducials 251, 252, & 253 are viewed.

FIG. 2B illustrates a top view of vertical fiducials in accordance with one embodiment of the present invention. Because vertical fiducials 251, 252, & 253 are viewed from directly overhead, centering vertical fiducial 252 appears directly in the center of both vertical reference fiducials 251 & 253. Here, vertical fiducials 251, 252, & 253 reside directly in a portion of base 210 as opposed to residing in a fiducial retainer.

FIG. 2C illustrates an offset top view of vertical fiducials in accordance with one embodiment of the present invention. Offsetting one's vantage or viewing perspective of vertical fiducials 251, 252, & 253 from directly overhead to a vantage point towards one side of centering vertical fiducial 252 results in the effect that centering vertical fiducial 252 appears closer to one vertical reference fiducial than to the other. In this example in FIG. 2C, centering vertical fiducial 252 appears closer to vertical reference fiducial 253 than to vertical reference fiducial 251. In this way, a physician can use the relative apparent distances of centering vertical fiducial between vertical reference fiducials 251 & 253 to "line up" or otherwise align a radiographic imaging device directly overhead or substantially perpendicular to procedure radiograph orientation device 200.

Visual or radiographic graduations or other markings may be added along the field of view of vertical fiducials 251, 252, & 253 to assist in determining the angle from which vertical fiducials 251, 252, & 253 are being viewed. Although vertical fiducials 251, 252, & 253 are depicted herein as vertical lines or wires, one skilled in the art with the benefit of this disclosure will appreciate that vertical fiducials 251, 252, & 253 may be of any suitable shape or profile to allow determination of the orientation or alignment of a radiographic imaging device. Additionally, other visual sighting or aiming devices or components may be included or used in conjunction with the devices herein to aid in the alignment of radiographic imaging devices.

FIG. 3A illustrates a cross-sectional view of an example of plurality of elongated support slats operably interacting via a tension cable. Tension cable 330 extends through elongated support slats 315 and spacers 325. FIG. 3B illustrates a perspective view of an example of one end of a support slat. In FIG. 3B, aperture 319 in elongated support slat 315 allows tension cable 330 to extend through support slat 315. Concave side 317 of elongated support slat 315 provides a curved surface adapted to pivot about spacer 315. Thus, as illustrated in FIG. 3C, concave side 317 of elongated support slat 315 is configured to interact with spacers 325. Apertures 319 allows a tension cable to extend through the thickness 316 of elongated support slat 315 and spacers 325.

Although the sides of elongated support slat 315 are depicted herein as substantially concave, one skilled in the art with the benefit of this disclosure will recognize that any myriad of shapes and surface contours could be used to interact with or pivot about spacer 325. Nor is the depiction of spacers 325 as substantially cylindrical intended to be limiting as to the shape of spacers 325. Spacers 325 may be formed in any shape suitable to allow support slats 315 to pivot about spacers 325.

Although tension cable 330 is depicted herein as extending through spacers 325, it is recognized that tension cable need not extend through spacers 325. In such an embodiment, spacers 325 may be held in place between the contours of the sides of elongated support slats 315.

Figure 4:
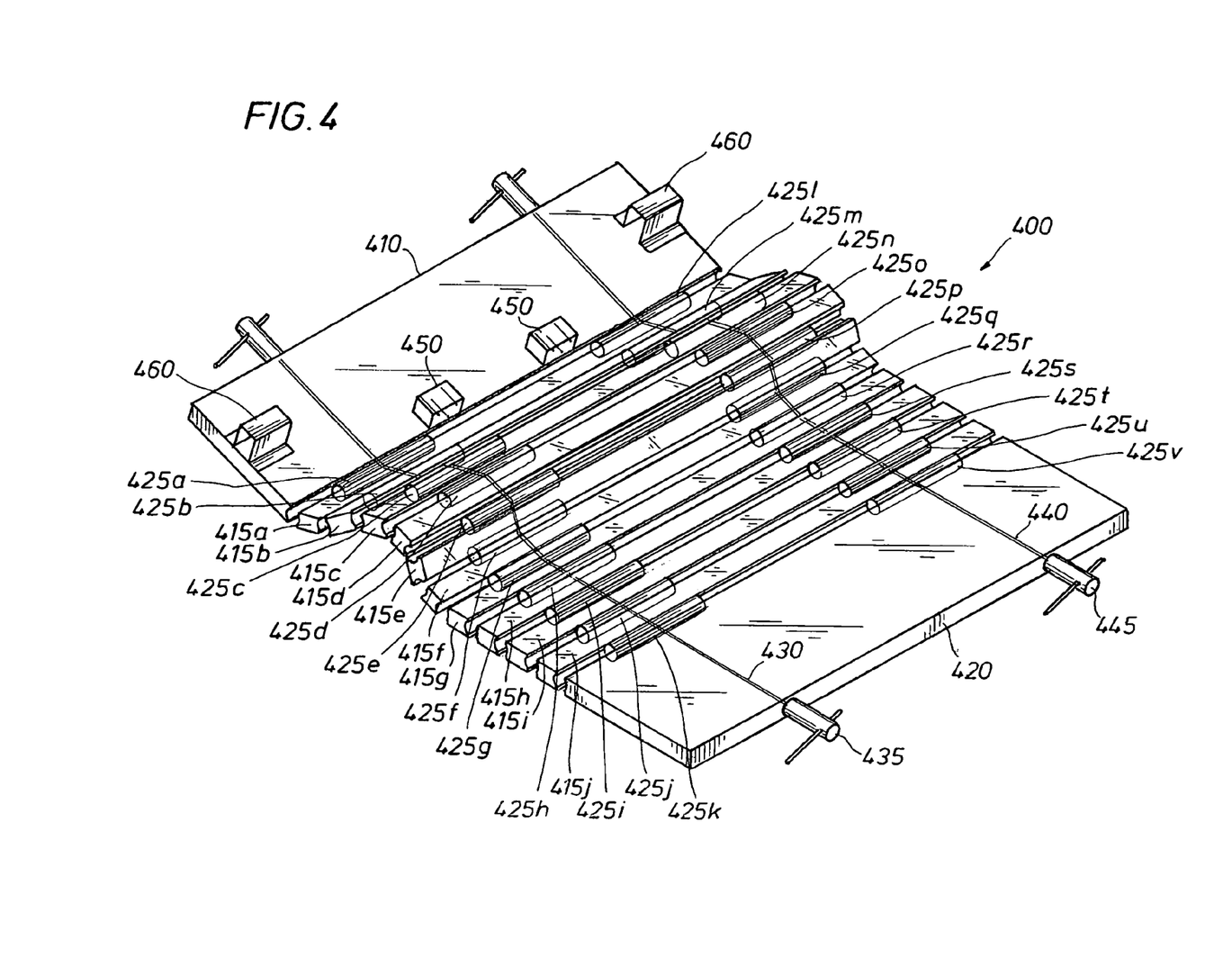
FIG. 4 illustrates a perspective view of an example of a procedure radiograph orientation device shown in a supporting orientation.

FIG. 4 illustrates a perspective view of an example of a procedure radiograph orientation device 400 shown in a supporting orientation. The term, "supporting orientation," as used herein, means any non-flat orientation of device 400 that is conducive to supporting a patient's anatomy in an orientation favorable to performing a medical or surgical intervention. Tension cables 430 & 440 extend through rostral base plate 410, elongated support slats 415a-415j, spacers 425a-425v, and caudal base plate 420.

Tension adjusters 435 & 445 may be used to adjust the tension of tension cables 130 & 140. A loose tension on tension cables 430 & 440 allows rostral base plate 410, elongated support slats 415a-415j, and caudal base plate 420 to pivot freely about spacers 425a-425v. Tension cables 430 & 440 may be increased to a tension sufficient to device 400 in a fixed orientation. The fixed orientation shown in FIG. 4 illustrates one example of a desired supporting orientation suitable for a patient undergoing certain types of cervical or other medical interventions. Device 400 is depicted here in an orientation adapted to allow a patient's head to be supported by rostral base plate 410 with the curvature of a patient's upper spine supported in a desired fixed orientation by elongated support slats 415a-415f.

Tension adjusters 435 & 445 may loosen the tension on tension cables 430 & 440 to release spine stabilizer device 400 from the fixed orientation depicted in FIG. 4. Alternatively, tension adjusters 435 & 445 may be loosened just enough to make an adjustment to the supporting orientation of spine stabilizer device 400 and then retightened to secure spine stabilizer device 400 once again in a fixed orientation.

As before, certain portions of procedure radiograph orientation device 400 may be radiolucent or radiopaque to provide radiographic reference landmarks to assist in the alignment and orientation of radiographic imaging devices. Here, rostral base plate 410, elongated support slats 415a-415j, caudal base plate 420, and spacers 425b, 425d, 425f, 425h, 425j, 425l, 425n, 425p, 425r, 425t, & 425v are substantially radiolucent. Vertical fiducials 450 and spacers 425a, 425c, 425e, 425g, 425i, 425k, 425m, 425o, 425q, 425s, & 425u ("horizontal fiducials") are substantially radiopaque. In this way, vertical fiducials 450 and horizontal fiducials 425a, 425c, 425e, 425g, 425i, 425k, 425m, 425o, 425q, 425s, & 425u provide radiographic reference landmarks for more precise orientation and alignment of external spine stabilizer device 400 when using radiographic imaging.

Vertical fiducials 450, which are offset a fixed distance from each other, may be used in conjunction with radiographic imaging to center a patient on spine stabilizer device 400 or to orient a radiographic imaging device with respect to device 400. Any other variety of radiographic markers may be used in conjunction with device 400 to provide additional radiographic reference landmarks. Additionally, for finer precision, additional fiducials may be positioned in multiple planes. To properly distinguish fiducials in one plane from fiducials residing in other planes, different fiducial shapes or profiles may be used. Additionally, it is recognized that in certain embodiments, vertical fiducials 450 may be adapted to slide across rostral base plate 410 or be otherwise movable to any portion of device 400, depending on the orientation and alignment needs of the particular medical intervention being performed.

Optional brackets 460 may be used as anchor or connection points to which a brace or other attachment device may be attached to center a patient's head or body. Other suitable components may be added or otherwise affixed to device 400 as required by the relevant medical procedure to be performed.

Figure 5:
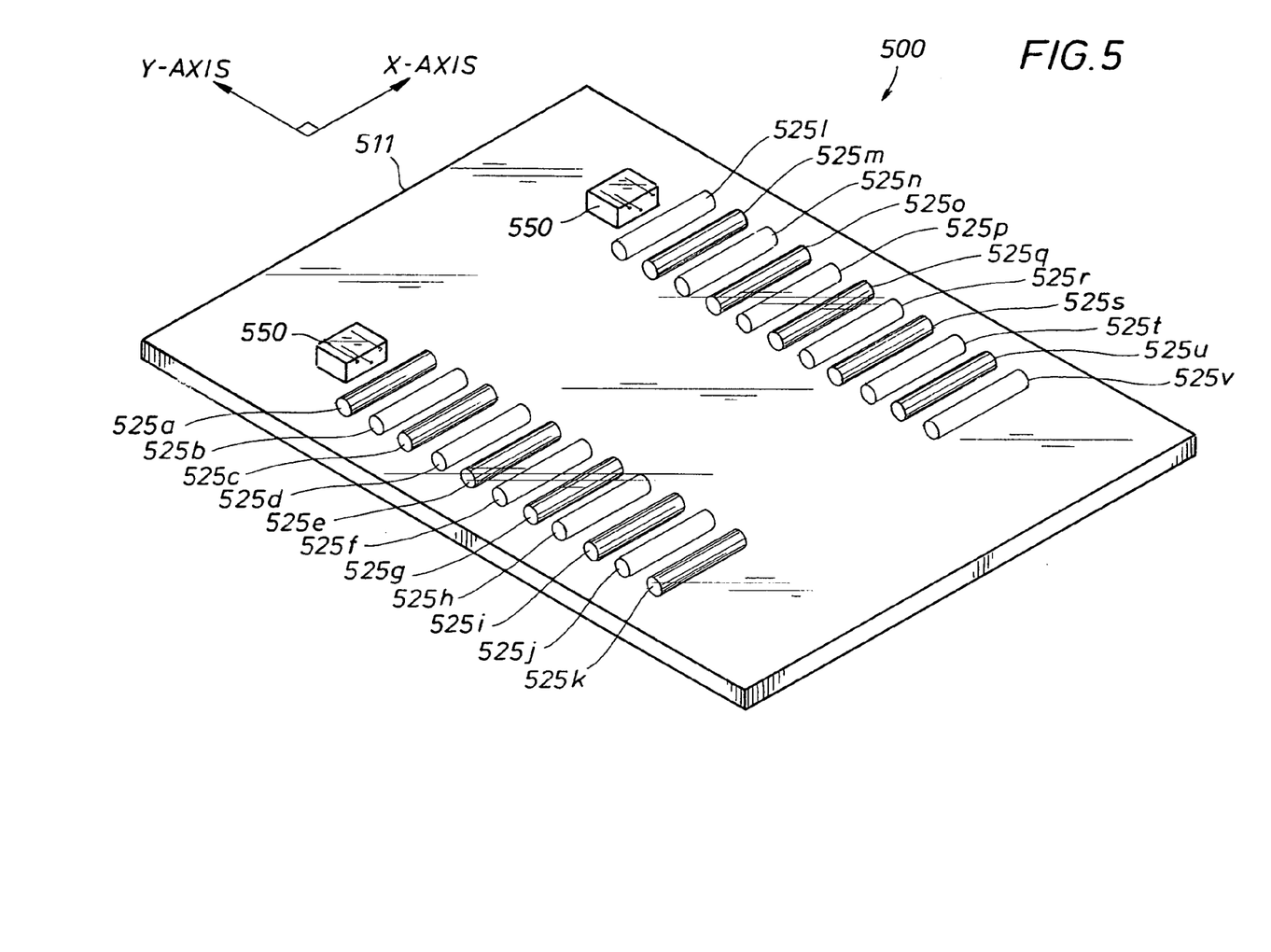
FIG. 5 illustrates an example of an interoperative radiographic aiming device.

FIG. 5 illustrates an example of an alternative embodiment of a procedure radiograph orientation device referred to herein as an interoperative radiographic aiming device. Interoperative radiographic aiming device 500 is a base plate that includes radiographic reference landmarks to assist in the alignment and orientation of radiographic imaging devices. Base plate 511 is a rigid plate upon which a portion of a patient's anatomy may be supported.

Base plate 511 is substantially radiolucent and therefore, does not substantially appear on radiographic images. Vertical fiducials 550 provide radiographic reference landmarks for relative alignment of radiographic imaging devices along an x-axis, whereas horizontal fiducials 525a, 525c, 525e, 525g, 525i, 525k, 525m, 525o, 525q, 525s, 525u provide landmarks for relative alignment along a y-axis. Optional spacers 525b, 525d, 525f, 525h, 525j, 525l, 525n, 525p, 525r, 525t, 525v are radiolucent and are not required in all embodiments.

Figure 6A:
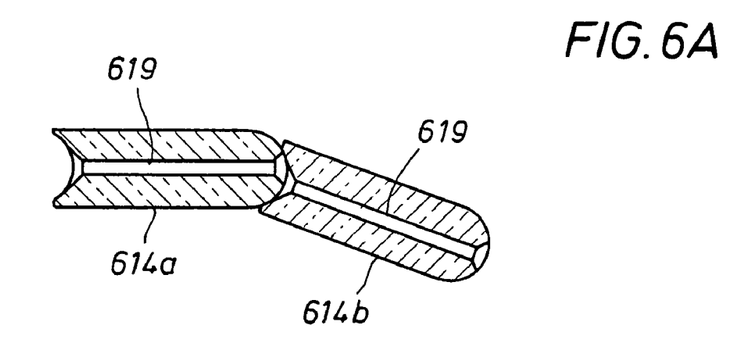
FIG. 6A illustrates a cross-sectional view of an alternative embodiment of elongated support slats with each slat capable of pivoting about adjacent elongated support slats.

FIG. 6A illustrates a cross-sectional view of an alternative embodiment of elongated support slats with each slat capable of pivoting about adjacent elongated support slats. Elongated support slats 614a & 614b comprise one elongated convex edge and one elongated concave edge and are thus adapted to pivot about one another when arranged adjacent one another. That is, convex edge of support slat 614a is adapted to pivot within the concave edge of support slat 614b. Aperture or hole 619 extends through elongated support slats 614a & 614b to allow the passage of a tension cable therethrough.

Successively arranged elongated support slats 614 (as shown below in FIG. 6D) may be used in lieu of the slat/spacer arrangement of previously depicted embodiments. In this way, spacers are not required in all embodiments of the present invention.

Figure 6B:
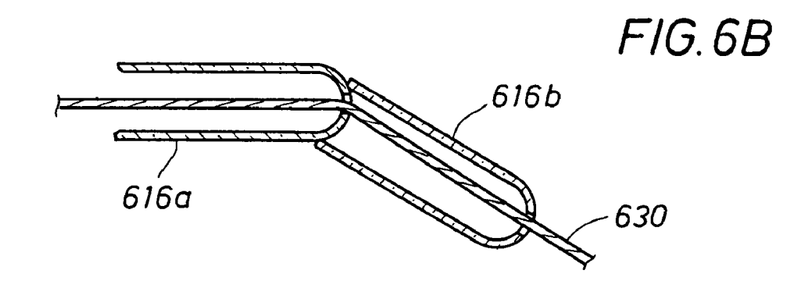
FIG. 6B illustrates a cross-sectional view of another alternative embodiment of elongated support slats with each slat capable of pivoting about adjacent elongated support slats.

FIG. 6B illustrates a cross-sectional view of another alternative embodiment of elongated support slats, with each support slat capable of pivoting about adjacent support slats. Elongated support slats 616a & 616b are substantially hollow and comprise one leading edge having a substantially convex shape. In this way, the substantially hollow elongated edge of support slat 616b is adapted to pivot about the elongated convex edge of elongated support slat 616a. Tension cable 630 extends through elongated support slats 616a & 616b.

Successively arranged elongated support slats 616 may be used in lieu of the slat/spacer arrangement of previously depicted embodiments.

Figure 6C:
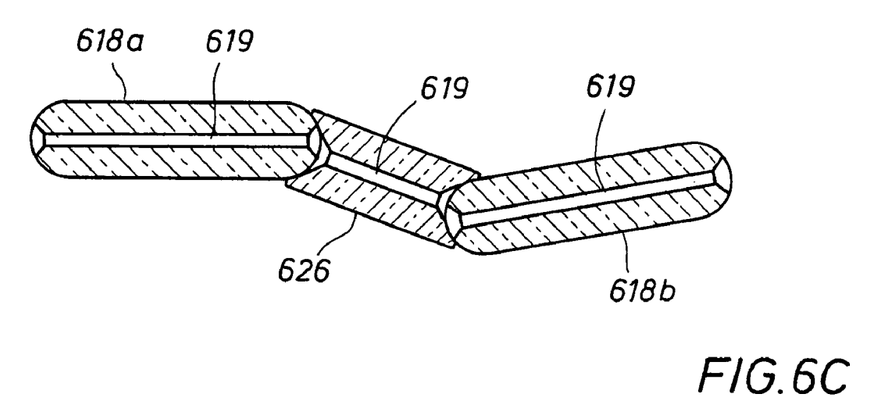
FIG. 6C illustrates a cross-sectional view of an alternative embodiment of a combination of elongated support slats and spacers.

FIG. 6C illustrates a cross-sectional view of an alternative embodiment of a combination of elongated support slats and spacers. Elongated support slats 618a & 618b are separated by spacer 626. Elongated support slats 618a & 618b have substantially convex edges and are thus adapted to interact with and pivot within the substantially concave edges of spacer 626. Aperture 619 extends through elongated support slats 618a & 618b and spacer 626 so as to allow passage of a tension cable therethrough. Elongated support slats 614 and spacers 626 may be formed of any shape suitable to allow adjacently arranged components to pivot about one another.

Figure 6D:
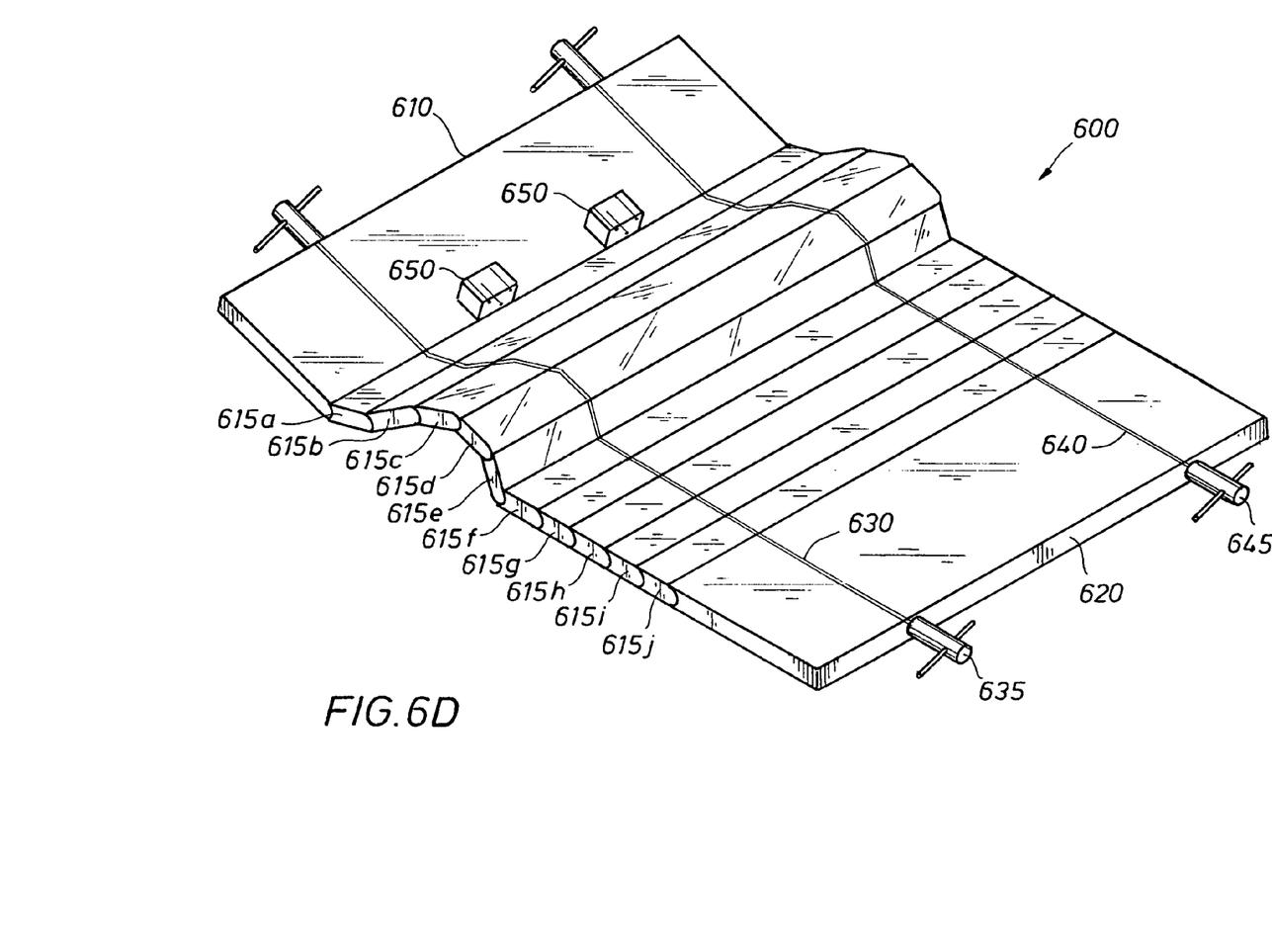
FIG. 6D illustrates a perspective view of an alternative embodiment of a procedure radiograph orientation device shown in a supporting orientation.

FIG. 6D illustrates a perspective view of an alternative embodiment of a procedure radiograph orientation device shown in a supporting orientation. Tension cables 630 & 640 extend through rostral base plate 610, elongated support slats 615a-615j, and caudal base plate 620. Elongated support slats 615 have edges formed so as to pivot about one another when arranged adjacent one another in succession.

Tension adjusters 635 & 645 adjust the tension of tension cables 630 & 640. As before, the tension of tension cables 630 & 640 may be increased to a tension sufficient to secure device 600 in a fixed orientation or loosened to release device 600 from the fixed orientation depicted in FIG. 6.

As before, certain portions of procedure radiograph orientation device 600 may be radiolucent or radiopaque to provide radiographic reference landmarks. Here, rostral base plate 610, elongated support slats 615a-615j, and caudal base plate 620 are substantially radiolucent. Vertical fiducials 650 are substantially radiopaque. In this way, vertical fiducials 650 provide radiographic reference landmarks for more precise orientation and alignment of device 600 when used in conjunction with radiographic imaging. Optionally, horizontal fiducials may be secured in or to any component of device 600 to provide additional radiographic reference landmarks.

It is explicitly recognized that the devices herein may also be incorporated into other devices including operating tables or any surface upon which a medical intervention or surgery for a patient may be performed including, non-human patients, such as domestic and wild animals.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method for stabilizing and orienting a patient and a radiographic imaging device for a surgical intervention comprising:

provi­ding a procedure radiograph orientation device comprising: an elongated rostral base plate having a first elongated edge and a second elongated edge with an aperture extending therebetween, wherein the second elongated edge thereof is adapted to receive at least partially a spacer; a caudal base plate having a first elongated edge and a second elongated edge with an aperture extending therebetween, wherein the second elongated edge thereof is adapted to receive at least partially a spacer; a plurality of elongated support slats, each elongated support slat having a first elongated edge and a second elongated edge with an aperture extending therebetween, wherein the first and second elongated edges are adapted to receive at least partially a spacer; a first tension cable extending through the apertures of the elongated rostral base plate, the plurality of elongated support slats, and the elongated caudal base plate; a first tension adjuster for adjusting a tension of the first tension cable; wherein the plurality of elongated support slats are arranged sequentially along the length of the first tension cable between the rostral base plate and the caudal base plate, the elongated support slat closest to the rostral base plate being a first support slat and the elongated support slat closest to the caudal base plate being a last support slat; a plurality of spacers wherein each spacer is disposed between each of the plurality of elongated support slats, between the rostral base plate and the first support slat, and between the last support slat and the caudal base plate; wherein one or more of the plurality of spacers are radiopaque, the one or more radiopaque spacers being referred to as horizontal fiducials; and a first vertical fiducial wherein the first vertical fiducial is radiopaque;

adapting the procedure radiograph orientation device to a supporting orientation;

adjusting the tension of the tension cable via the tension adjuster so as to secure the procedure radiograph orientation device in the supporting orientation; and radiographically imaging a portion of the procedure radiograph orientation device.

2. The method of claim 1: wherein one or more of the plurality of spacers are radiopaque, the one or more radiopaque spacers being referred to as horizontal fiducials; and a first vertical fiducial secured to one of the following: the rostral base plate, the caudal base plate, and at least one of the elongated support slats, wherein the first vertical fiducial is radiopaque.

* * * * *